United States Patent
Kemeny

(12) 
(10) Patent No.: US 6,992,232 B1
(45) Date of Patent: Jan. 31, 2006

(54) ADHESIVE BANDAGE AND PACKAGING FOR ONE-HANDED PLACEMENT

(76) Inventor: Emanuel S. Kemeny, 1400 S. Joyce St. Apt. 602, Arlington, VA (US) 22202

( * ) Notice: Subject to any disclaimer, the term of this patent is extended or adjusted under 35 U.S.C. 154(b) by 0 days.

(21) Appl. No.: 11/142,397

(22) Filed: Jun. 2, 2005

(51) Int. Cl.
*A61F 13/00* (2006.01)
*A61F 15/00* (2006.01)

(52) U.S. Cl. ............................ 602/41; 602/43; 602/52; 602/54; 602/57; 602/58

(58) Field of Classification Search ................. 602/41, 602/42, 43, 52, 53, 54, 57, 58; 128/888, 128/889
See application file for complete search history.

(56) References Cited

U.S. PATENT DOCUMENTS

| | | | | |
|---|---|---|---|---|
| 2,273,873 A | * | 2/1942 | Klein .......................... | 128/888 |
| 2,280,506 A | * | 4/1942 | Betts .......................... | 128/894 |
| 5,086,763 A | * | 2/1992 | Hathman ..................... | 602/42 |
| 5,230,119 A | * | 7/1993 | Woods et al. ............... | 15/209.1 |
| 5,891,074 A | * | 4/1999 | Cesarczyk ................... | 602/42 |
| 5,916,225 A | * | 6/1999 | Kugel ......................... | 606/151 |
| 6,203,512 B1 | * | 3/2001 | Farris et al. ................. | 602/79 |
| 6,225,522 B1 | * | 5/2001 | Schroeder ................... | 602/57 |
| 6,596,917 B2 | * | 7/2003 | Oyaski ........................ | 602/43 |

FOREIGN PATENT DOCUMENTS

WO   WO 94/06382   * 3/1994

* cited by examiner

*Primary Examiner*—Henry Bennett
*Assistant Examiner*—Amanda Wieker

(57) ABSTRACT

An adhesive bandage allows one-handed (single-finger) lifting and placing, whereby the bandage can be quickly lifted from a supply container and accurately placed on a skin wound. The bandage consists of a tape whose upper surface has a finger-spot adhesive, and whose lower surface has adhesive for skin adhesion, and has a compressible-resilient pad for determinate pressure on a bleeding wound. Recessed embodiments are also taught. A tabbed-tissue is adhered to the bandage top as a separator in a supply container with a plurality of bandages, the tab useful as an alternative for lifting and placing the bandage.

4 Claims, 1 Drawing Sheet

ADHESIVE BANDAGE AND PACKAGING FOR ONE-HANDED PLACEMENT

BACKGROUND OF THE INVENTION

1. Field of the Invention

The invention is in the field of adhesive bandages and their packages, more specifically for one-handed placement and pre-determinate pressure on bleeding skin wounds.

2. Description of Prior Art

Adhesive bandages, and their packages, have been known in prior art for many years, perhaps the best known brand BAND-AID™ marketed by Johnson & Johnson. In general, such bandages consist of a non-rigid bandage tape which may be rectangular or circular in shape, with the skin-contact side being coated with a sticky adhesive, to which a centrally-located pad is attached to be placed on a skin wound, the periphery adhesive to be pressed to the skin surrounding the wound. Often, each bandage is individually enclosed in sterile protective tissues which are weakly cohesive or adhesive.

For such bandages, two hands are required to accurately remove the protective tissue and place the bandage on the wound.

Other adhesive bandages provide further concepts and materials, some of particular interest for the present invention and included hereunder by reference:

U.S. Pat. No. 6,124,522, to Mark Schroeder, provisional filed Nov. 24, 1998, teaching one-handed application of adhesive bandages using applicator tissue sheets, and a matchbook form of assemblage packaging;

U.S. Pat. No. 4,377,159, to Paul E. Hansen, filed Jun. 29, 1981, teaching pressure-pad bandages to provide localized pressure to a bleeding skin wound;

U.S. Pat. No. 2,280,506, to Richard T. Betts, filed Mar. 10, 1941, teaching an adhesive bandage strip with a cushioning pad to prevent pressure on foot wounds, the pad confined in a recess in the strip, the recess forcibly kept in form to prevent excess spreading of the pad under pressure.

Materials known in prior art adhesive bandages, and useful for the present invention, include: Bandage strip of PVC foam, or polyurethane, or cotton-nylon; Adhesives of acrylics and latex; and Pads of compressible-resilient foams using polyurethane, polyolefin, and the like, supplied by the 3M™ Company. These teachings are found in the prior art listed above, which are incorporated herein by reference.

SUMMARY OF THE INVENTION

Three embodiments of the novel adhesive bandage are disclosed, which allow one-handed (single-finger) lifting and placing, whereby the bandage can be quickly lifted from a supply container and accurately placed on a skin wound. The basic embodiment bandage consists of a tape whose top surface has a finger-spot adhesive for finger-lifting, and whose bottom surface has periphery adhesive for skin adhesion, and a compressible-resilient pad for determinate pressure on a bleeding wound. Two recessed embodiments are disclosed, one with a recessed pad to provide determinate pressure, and the other with recessed pad and recessed finger-spot adhesive. A tabbed-tissue is adhered to the bandage top as a separator in a supply container with a plurality of bandages, the tab useful as an alternative for lifting and placing the bandage. Further, the bandages and/or tissues may be slightly larger that the container so as to weakly jam against the container walls to form a friction seal when loaded into the container from the top or the bottom, and thereby provide security for container-angled removal, and protection from foreign falling matter.

DETAILED DESCRIPTION OF EMBODIMENTS

Figure 1:
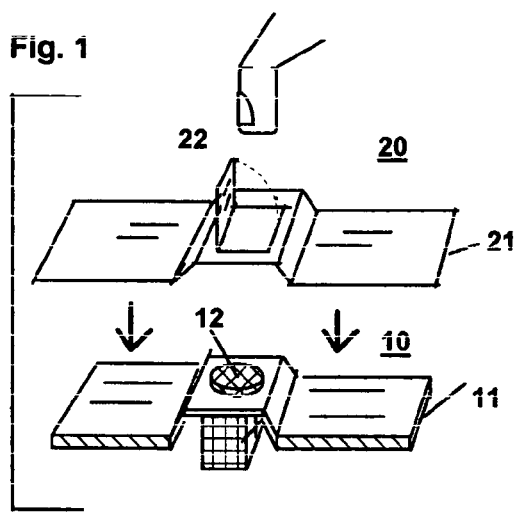
FIG. 1 is a perspective view of a recessed-pad embodiment of the inventive bandage, shown paired with its tabbed-tissue cover, and finger-lift mode.
Figure 2:
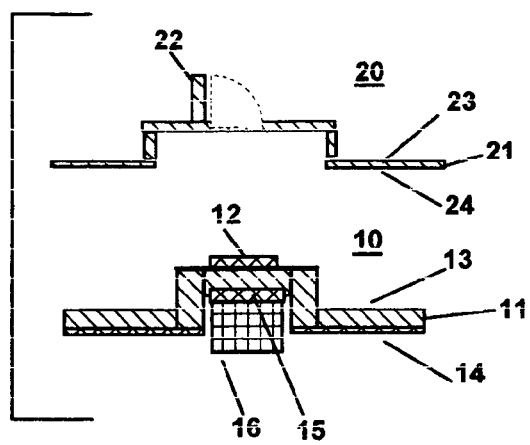
FIG. 2 is a side view of the paired embodiment shown in FIG. 1.

Referring to FIG. 1, this perspective view shows one embodiment of inventive bandage 10 paired with its tabbed-tissue 20. The paired elements are shown separated for clarity. FIG. 2 is a side view corresponding to FIG. 1, showing further details, specifically bandage 10 comprising tape 11, whose upper surface periphery 13 is bare except for the finger-spot of strong adhesive 12, and whose lower surface periphery 14 is coated with a strong adhesive for skin adhesion. In this embodiment, tape 11 is formed to provide an underside recess for strong adhesive 15 holding compressible-resilient pad 16. Pad 16 is preferably 50% within the recess.

FIG. 2 further shows tabbed-tissue 20 comprising tissue sheet 21, formed to mate with the top of bandage 20 to form a bandage-tissue pair, upper surface 23 is non-stick, and lower surface periphery 24 is coated with a weak adhesive of strength sufficient to lift bandage 10 when adhered to surface 13. Tab 22 is a semi-circle cut in tissue 21, pulled open to expose finger-spot adhesive 12. One-hand lifting can be done one finger on finger-spot 12 or by two fingers on tab 22. Tab 22 is non-stick. The tissue 20 is peeled from tape 10 with twisting pull.

Figure 3:
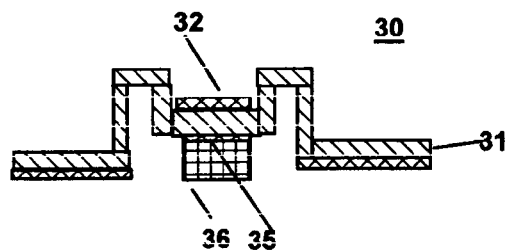
FIG. 3 is an embodiment of the inventive bandage with recessed pad and finger-adhesive.

FIG. 3 shows another embodiment in which bandage 30 (as a modification of bandage 10) comprises tape 31 with two formed cavities: one underside cavity for pad-adhesive 35 with compressible-resilient pad 36, and one upperside cavity for finger-spot adhesive 32.

It is noted that a third embodiment of the inventive bandage (not illustrated) is essentially the bandage 10 with no recess.

Figure 4:
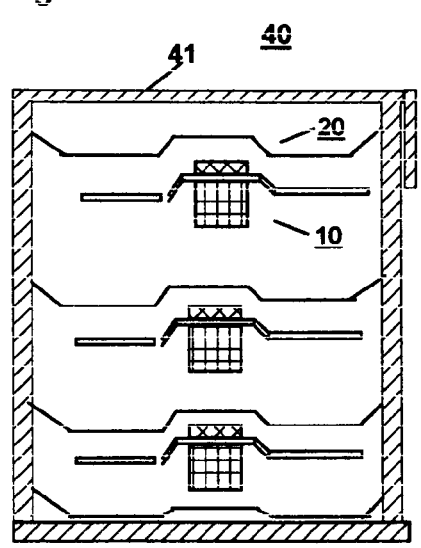
FIG. 4 is a cross-section view of a container box in which bandage-tissue pairs are stored.

FIG. 4 shows container 40, comprising cover 41 which when lifted exposes a plurality of stored items comprising pairs of bandage 10 and tabbed-tissue 20. The paired elements are shown separated for clarity.

Note 1: The bandages and/or tabbed tissues may be made slightly larger than the container and loaded from the top or bottom of the container so as to jam fit into the container, sufficiently secure to allow removal of bandage-tissue pairs one pair at a time, and forming a wall-friction seal against contaminants falling into the container.

Note 2: The compressible-resilient pad if partially recessed can provide a determinate pressure on a wound when compressed to be flush with the tape bottom surface. For minor wounds a pressure of 2 ounces for children, and 20 ounces for adults has been found practical.

Note 3. Compressible Pad 16 is preferably 50% exposed ouside the tape recess, such that upon placement and compressed to its maximum possible flush with the tape, the pad approximates a determinate pressure on the wound.

Note 4. Finger-spot adhesive 12 in FIG. 2 is unshielded and removable by finger rubbing. Finger-spot adhesive 32 in FIG. 3 is shielded as recessed.

Note 5: The tabbed-tissue with surface 24 adhered to the bandage tape periphery 13 can help stiffen the tape to prevent droop.

Note 6. The bandage-tissue pairs may be inserted into the container from the top or bottom to determine the tissue directional bend and drag for removal.

I claim:

1. An adhesive bandage for accurate one-handed single-finger placement on skin wounds, comprising:
   (a) a bandage tape comprising a top surface and a bottom surface;
   (b) said top surface containing a finger-adhesive spot of sufficient size and stickiness to adhere to a human finger,
   (c) said bottom surface containing a pad-adhesive spot, to which a pad is securely adhered,
      (i) said pad-adhesive spot and pad aligned directly opposite said finger-adhesive spot,
      (ii) said bottom surface further containing a periphery adhesive for adhesion to skin around a wound,
   (d) said bandage tape of semi-rigid stiffness sufficient to resist droop when suspended by said human finger, whereby said adhesive bandage, using a single human index finger, can be lifted and the pad accurately and directly pressed on a skin wound, after which the tape periphery can be pressed by adjacent fingers to force adherence to the skin around the wound.

2. The adhesive bandage of claim 1, further comprising:
   (e) a recess formed in said bottom surface of the bandage tape, the recess containing said pad-adhesive and pad, said pad partially submerged within said recess and partially exposed, said pad made of compressible-resilient material such that, when the pad is pressed to a skin wound and compressed flush with the bandage surface, the pad provides a pre-determinate value of pressure on the wound to minimize bleeding, while said adjacent fingers force adherence of the tape around the wound.

3. The adhesive bandage of claim 1, further comprising:
   (f) a recess formed in said top surface of the bandage tape, the recess containing said finger-adhesive such that the adhesive is shielded from external matter.

4. A packaging system for one-handed placement adhesive bandages, comprising:
   (a) a container for storing a plurality of bandage-tissue pairs,
   (b) each bandage-tissue pair comprising an adhesive bandage comprising:
      (i) a bandage tape comprising a top surface and a bottom surface;
      (ii) said top surface containing a finger-adhesive spot of sufficient size and stickiness to adhere to a human finger;
      (iii) said bottom surface containing a pad-adhesive spot to which a pad is securely adhered, said bottom surface further containing a periphery adhesive for adhesion to skin around a wound,
      (iv) said bandage tape of semi-rigid stiffness sufficient to resist droop when suspended by said human finger,
   (c) each bandage-tissue pair further comprising a tabbed tissue to top-cover the bandage, said tabbed tissue comprising:
      (i) a tissue sheet slightly larger than the bandage,
      (ii) the tissue sheet having a semi-circle cut to form a tab,
      (iii) the tissue formed to fit as a cover on the bandage,
      (iv) the tissue underside periphery coated with a weak adhesive, the tab itself non-stick,
      (v) the tissue upper surface non-stick,
   (d) the tissue underside periphery adhered to the bandage top to form said bandage-tissue pair,
      whereby a plurality of bandage-tissue pairs are jammed into the container, the oversize tissue forced against the container wall to form a friction seal, and with the container top open, each bandage-tissue pair may be lifted by its finger-adhesive spot or tissue tab.

* * * * *